(12) United States Patent
van Moorlegem et al.

(10) Patent No.: US 6,776,771 B2
(45) Date of Patent: Aug. 17, 2004

(54) ADAPTIVE BALLOON WITH IMPROVED FLEXIBILITY

(75) Inventors: Wilfried Franciscus Marcellinus van Moorlegem, Lubbeek (BE); Petrus Antonious Besselink, Enschede (NL)

(73) Assignee: Tuborg Engineering, Lubbeek (BE)

( * ) Notice: Subject to any disclaimer, the term of this patent is extended or adjusted under 35 U.S.C. 154(b) by 31 days.

(21) Appl. No.: 09/952,332

(22) Filed: Sep. 14, 2001

(65) Prior Publication Data

US 2002/0049408 A1 Apr. 25, 2002

Related U.S. Application Data

(60) Provisional application No. 60/232,382, filed on Sep. 14, 2000.

(51) Int. Cl.[7] .............................................. A61M 29/00
(52) U.S. Cl. .............................. 604/101.01; 604/103.02
(58) Field of Search ............. 604/96.01, 101.01–101.02, 604/101.04–101.05, 103.01–103.02, 103.06–103.07, 915, 916, 919; 606/192–194

(56) References Cited

U.S. PATENT DOCUMENTS

| 4,183,102 A | | 1/1980 | Guiset |
| 4,546,759 A | * | 10/1985 | Solar .......................... 600/18 |
| 4,581,017 A | | 4/1986 | Sahota |
| 4,762,130 A | * | 8/1988 | Fogarty et al. ............. 606/159 |
| 4,909,252 A | | 3/1990 | Goldberger |
| 5,002,532 A | | 3/1991 | Gaiser et al. |
| 5,003,989 A | | 4/1991 | Taylor et al. |
| 5,019,042 A | * | 5/1991 | Sahota ................... 604/101.01 |
| 5,395,333 A | | 3/1995 | Brill |
| 5,415,635 A | | 5/1995 | Bagaoisan et al. |
| 5,613,948 A | | 3/1997 | Avellanet |
| 5,716,340 A | | 2/1998 | Schweich, Jr. et al. |
| 5,951,514 A | | 9/1999 | Sahota |
| 6,022,359 A | * | 2/2000 | Frantzen ...................... 606/108 |
| 6,126,634 A | | 10/2000 | Bagaoisan et al. |
| 6,146,358 A | * | 11/2000 | Rowe ..................... 604/103.02 |
| 6,193,686 B1 | | 2/2001 | Estrada et al. |

FOREIGN PATENT DOCUMENTS

WO    WO 99/40962    8/1999

* cited by examiner

*Primary Examiner*—Loan H. Thanh
(74) *Attorney, Agent, or Firm*—Dinsmore & Shohl LLP

(57) ABSTRACT

A balloon for use in surgical procedures, such as angioplasty. The balloon is configured as a balloon catheter with an axial series of segmented chambers, each connected to a tubular core that is adapted to a transport a pressurizable fluid source. The chambers are made of an elastically expandable material that inflates in response to the introduction of a pressurized fluid source. Each chamber includes a body lumen inner wall engaging surface and a pair of generally opposed flanges. Flexibly compliant links are disposed between adjacent chambers. These links may be integral with the flanges, or may constitute a separate hinge that couples the chambers at least to the central core. As the balloon is routed through a body lumen, curvature in the lumen is mimicked by the balloon, as it is able to flexibly conform to the shape of the lumen path by preferential bending at the flexibly compliant links.

8 Claims, 3 Drawing Sheets

ADAPTIVE BALLOON WITH IMPROVED FLEXIBILITY

CROSS REFERENCE TO RELATED APPLICATIONS

This application claims the benefit of U.S. Provisional Application 60/232,382, filed Sep. 14, 2000.

BACKGROUND OF THE INVENTION

During a typical percutaneous transluminal coronary angioplasty (PTCA) procedure, a balloon catheter is transported to a stenotic region in an artery or related body lumen. Normally a balloon for PTCA has an oblong, cylindrical shape with a single chamber that can be inflated to open up the arterial passageway. Once the lumen has been opened up, the balloon is deflated and removed through the same path by which it entered. If an uninflated balloon is to be easily placed inside and transported through an anatomical lumen, such as a curved artery, it must be flexible enough to be able to follow the lumen curvature, while maintaining enough rigidity to avoid bunching up during its passage to the desired endoluminal location. Conventionally, a relatively rigid guide wire can be used to effect balloon placement. Once the balloon has been inflated, its flexibility problem becomes much more profound, as the balloon is now often too rigid to bend in conformance with the lumen wall. Such a balloon will have the tendency to straighten itself upon inflation, thus creating undesirable forces on the inner wall of the lumen.

In some situations, the chance for restenosis of a body lumen that has been dilated can still be great. To avoid the necessity of repeated PTCA procedures, the doctor will implant an endoluminal prosthesis, also known as a stent, into the patient's body lumen adjacent the stenotic region. The stent is intended as a permanent or semi-permanent structure that maintains an open passageway, thereby reducing the chance for restenosis. Typically, the stent is balloon expandable, and is mounted around the balloon, such that both can be inserted simultaneously. If the stent has to be placed into a curved section of the body lumen, it too will take this straightened shape from the expanding single chamber balloon, which could lead to possible puncture or similar damage to the lumen wall. Additionally, the inappropriate fit between stent and lumen wall could allow the stent to loosen and migrate to a different part of the lumen.

Rigid expansion of the balloon can cause other problems to occur as well. For example, during angioplasty, the balloon is inflated to such an extent that the lumen in which the balloon is placed becomes temporarily plugged. While this is not critical for rapid angioplasty or stent deployment procedures, or is not feasible with very small or very high pressure devices (such as in a carotid artery, where the lumen diameter is typically between 2.5 and 4 millimeters), it is of concern for devices used in larger cross-sectional area lumens, such as a patient's leg or aorta, where lumen diameters can be from approximately 8 to 25 millimeters. If the inflated balloon obstructs blood flow for too long (typically for more than a few seconds), permanent damage to downstream organs can occur due to ischemia, which is the cessation of blood flow through the lumen. Accordingly, it is often desirable to keep the patient's blood flowing through the lumen while the balloon is in the inflated state. This is preferable to cycling the balloon between an inflated and deflated state, as such action can place additional stress on an already compromised lumen wall.

Multiple chamber balloons have been introduced into the art to meliorate the difficulty in transporting relatively rigid catheters into body lumens with tortuous paths. For example, U.S. Pat. No. 5,019,042 to Sahota, and U.S. Pat. No. 5,415,635 to Bagaoisan et al. both describe multiple lobed balloon catheters that have one set of lobes that expand more than other sets. Similarly, the introduction of perfusion balloons, so named because of an open channel that extends through or around the balloon to permit continuous flow of blood, has partially solved the ischemia dilemma. Examples of perfusion balloons are described in U.S. Pat. No. 5,613,948 to Avellanet, and U.S. Pat. No. 4,909,252 to Goldberger, both of which include a perfusion channel extending axially through a single-chamber balloon with eccentrically mounted expansion fluid supply. There have additionally been attempts to combine perfusion features with flexible, multiple chamber balloons, as evidenced by some of the aforementioned patents. However, the size of the apertures leading into and out of the perfusion channel is such that blood throughput can be unacceptably low, which limits the amount of time the doctor has to perform the PTCA procedure, as well as create a pressure gradient that could assist in pushing the balloon farther downstream than intended. In addition, the relatively large profile of the uninflated assembly makes transport through small or highly curved body lumens difficult, while the multiple layers found in present balloon catheter construction make for expensive, damage-prone devices.

What is needed is a balloon catheter that can be hinged while inflated to better conform to the shape of the lumen in which it is disposed. What is additionally needed is a flexibly compliant balloon catheter that can mimic the shape of a path formed by a body lumen while the catheter is uninflated, thereby enhancing the ability of the catheter to be inserted into curved, tortuous lumen paths. What is furthermore needed is a balloon catheter of such construction that fabrication difficulties and susceptibility to damage are meliorated. What is also needed is a flexible balloon catheter that can maintain blood perfusion, even when the catheter is in its inflated configuration, and even when disposed in a curved or tortuous part of a body lumen.

SUMMARY OF THE INVENTION

These needs are met by the present invention, whereby a flexible balloon catheter according to the present invention is made of a series of short inflatable chambers in fluid communication with one another through connection to a common core that can transport a pressurized fluid to the chambers. In the context of the present invention, the term "flexible" and its variants is meant to convey that it is easier for the balloon (either expanded or unexpanded) to bend in flexure, or normal to its axial dimension, while traversing a curved body lumen than it would be if the multiple chambers and compliant link/hinge sections herein described were not employed. Similarly, the terms "inflatable", "expandable" and their variants are used interchangeably throughout this disclosure to describe the ability of the balloon (and its separate chambers) to enlarge in response to the presence of a pressurized fluid. Even upon balloon inflation, the connections between the balloon's numerous short chambers remain compliant enough to follow the natural curvature of the lumen, without other forces than radial pressure against the inner wall of the artery. Balloon insertion through the tortuous paths associated with anatomical lumen becomes much more reliable, thereby significantly reducing the risk for damaging the lumen. Further, when the balloon is used in conjunction with a prosthetic stent, it becomes possible to place a longer stent in such a curved lumen, with the added assurance that after inflation the stent will be deployed following the natural curves of the lumen.

It is therefore an object of the invention that a balloon for angioplasty is made in short sections (or chambers) compliantly linked therebetween in order to improve the flexibility and adaptability in both the deflated as well inflated state such that the tendency of the sectioned balloon to straighten during inflation is reduced, thus improving its insertability into a curved body lumen.

It is a further object of the present invention to vary the length of the compliant links between each of the chambers so that flanges that make up the chamber side walls need not be spaced substantially parallel to its immediate neighbor on an adjacent chamber, thus permitting additional axial room, and hence flexibility, without changing the outer geometry of the inflated balloon assembly.

It is still another object of the present invention to provide a balloon catheter that includes a series of discrete ring- or donut-shaped balloon chambers, each with a large central aperture and mounted on a common pressurizable fluid delivery core, thus allowing blood perfusion through the center of the balloon in both its uninflated and inflated states.

It is an additional object of the present invention to provide a perfusion balloon made up of discrete chambers that individually include a perfusion aperture and together make up a substantially flexible, hollow perfusion canal that can allow at least one other additional catheter to pass therethrough to be used for a different procedure such as for distal protection against emboli, for distal angioplasty and/or stenting, for pressure monitoring or any other related treatment, or additional treatment methods, such as ultrasonic, radiation, laser, thermal or related procedure.

It is still another object of the present invention that individual balloon sections of a flexible balloon catheter are covered with a flexible liner or sleeve to tailor surface smoothness, reduce the deflated size, control the friction between the sleeve and an inserted stent, increase the speed of deflation, control the timing of inflation over the length or influence the final dimensions during and after inflation, or to get a more even radial pressure to a lumen wall.

An additional object of the present invention is that the outer wall of the segmented perfusion balloon or the liner or sleeve surrounding the individual balloon chambers is provided with drugs that can be released with a controlled speed in order to treat the inner wall of the lumen locally during a given period.

Yet another object of the invention is the production of segmented balloons by sealing two layers of polymer sheet in a specific pattern, which determines the dimensions, position, and flexibility of the final inflatable and non-inflatable sections. Parts of the sealed sections can be cut away to create hinges for additional flexibility.

Another object of the invention is to provide a segmented balloon catheter where the dimensions and arrangement of the connecting channels between the adjacent donut-shaped balloon chambers are chosen so that inflation of the device performs in a gradual way, where an inflation gradient runs from the proximal to the distal end, which can permit the placement of a stent to also become more gradual and therefore controllable when combined with such a segmented balloon.

According to a first embodiment of the invention, a balloon for use as a surgical device in a body lumen is disclosed. The balloon includes an axially elongate tubular core with a plurality of expandable chambers disposed on the outer surface thereof, and a plurality of flexibly compliant links disposed between adjacent chambers. The core is further defined by a proximal end configured to be in fluid communication with a pressurizable fluid source, and a distal end. The hollow central region of the tubular core extends between the proximal and distal ends, and includes a plurality of apertures disposed on its outer radial surface such that each aperture defines a fluid communication path between the hollow central region and the outer surface of the core. The apertures are configured such that they are substantially axially spaced upon balloon expansion. As used in conjunction with the present disclosure, the term "substantially" refers to an arrangement of elements or features that, while in theory would be expected to exhibit exact correspondence or behavior, may, in practice embody something slightly less than exact. For example, the enhanced flexibility of the present invention balloon catheter in its inflated condition allows the outer surface of the catheter to "substantially" engage the inner wall of a body lumen into which it is placed, even if the lumen is curved or irregular. Thus, by substantially engaging the lumen inner wall, a majority of the catheter's outer surface designed to contact the lumen inner wall will in fact do so upon proper insertion and inflation, rather than establishing contact at only a few discrete places. The chambers are disposed on the outer surface of the tubular core such that each chamber is in fluid communication with the hollow central region through at least one of the radial apertures. The flexibly compliant links connect each of the chambers to one another as well as to the outer surface of the tubular core. The flexibly compliant links, which may comprise the portion of the core disposed between adjacent chambers or be a separate hinge structure mounted onto the core, by virtue of their small cross-sectional profile relative to the expanded chambers, effect improved flexibility of the balloon by breaking up the rigidity of an otherwise single elongate chamber.

Optionally, the sections making up the flexibly compliant links or hinges can be made longer or shorter to tailor the flexibility to specific needs. In situations where the flexibly compliant link is a hinge, the hinge may be an integral, continuous connection between adjacent chambers, or fabricated from joined disparate members. Preferably, the material used for the chambers and hinges is of substantially constant thickness throughout. Each of the plurality of chambers can be defined by an outer surface that comprises a body lumen inner wall engaging portion and a pair of flange portions that extend between the body lumen inner wall engaging portion and one of the hinges. In addition, the individual chambers can be enveloped within a flexible sleeve to promote a uniform expanded profile. In the present context, the radially outward surface of each chamber, referred to herein as the "body lumen inner wall engaging portion" (and minor variants thereof) is defined to include not only direct surface-to-surface contact between this surface and the lumen inner wall, but also where an optional sleeve (discussed in more detail below) is placed around one or more of the chambers to prevent direct contact, as long as such addition is not significantly disruptive of the ability of those chambers to expand the lumen in accordance with their PTCA function. As another option, each of the hinges can possess an axial length such that upon balloon inflation, opposing flanges between axially adjacent chambers are substantially parallel to one another. In the alternative, the hinges possess an axial length such that, upon inflation of the balloon, opposing flange portions between axially adjacent chambers are farther apart near the body lumen inner wall engaging portion than they are near the hinge. As another alternative option, the hinges possess an axial length such that, upon balloon inflation, opposing flange portions between axially adjacent chambers are farther apart near the hinge than they are near the body lumen inner wall engaging portion. Moreover, drugs (such as restenosis inhibitors), a stent device and a chamber-enveloping sleeve, or any combination of the three, may optionally be included.

According to a second embodiment of the invention, a surgical device assembly for insertion into a body lumen is disclosed. This embodiment includes, in addition to the features of the previous embodiment, a guide wire configured to assist in transporting the balloon through the body lumen; and an expandable stent disposed over the balloon. This stent can balloon expandable or self-expanding, the latter including shape-memory materials such as nickel-titanium. Also, the axially elongate tubular core and expandable chambers can be made from a single piece of material. As with the first embodiment, drugs (such as restenosis inhibitors), a stent device and a chamber-enveloping sleeve, or any combination of the three, may optionally be included.

According to a third embodiment of the invention, a perfusion balloon for use as a surgical device is disclosed. The balloon includes a plurality of expandable ring (or donut)-shaped chambers configured to be substantially axially aligned upon inflation, a chamber connecting channel is coupled to the plurality of chambers, and a hollow central region extending from a proximal end to a distal end of the balloon. Each of the chambers includes a flange portion made up of a proximal flange and a distal flange that are substantially axially aligned with one another when the chamber is expanded, as well as a generally circumferential body lumen inner wall engaging portion disposed between the proximal and distal flanges of the flange portion. A proximal end of the channel is configured to be in fluid communication with a pressurizable fluid source. Inherent in any ring-like structure is a centrally disposed aperture; in the present embodiment, the centrally disposed aperture of each of these ring-shaped chambers allows blood perfusion therethrough, even during full balloon inflation. Such a design combines the feature of improved axial adaptability with the low resistance to blood flow to promote treatment without the dangers of occlusion. Moreover, the risk of undesirable axial displacement of the balloon by the blood pressure is reduced, since there is not a large pressure drop along the length of the balloon. In addition, due to the radially outward pressure exerted by the blood perfusion, the balloon may stay inflated for longer periods.

Optionally, the chamber connecting channel is integral with the chambers, thus resulting in simplified, one-piece construction between the two. Another option is that the perfusion balloon includes numerous balloon interchamber webs, each disposed between and coupled to adjacent chambers such that the webs provide enhanced balloon flexibility. In addition, each of the webs can be fluidly isolated from the pressurizable fluid source. The flexibility of the balloon can be further enhanced by radially projecting cutouts taken from the web. As with previous embodiments, the flexibility can be tailored by varying the axial length and geometry of the web. Additionally, the dimensions of the connecting channel can be configured to promote an inflation gradient between the proximal and distal ends of the balloon, thereby providing axial variations in the amount of expansion between chambers. In addition, the interconnection of the individual chambers is accomplished by direct coupling of the channel, rather than through a hinge. As another option, the relatively large perfusion canal, made up of the individual perfusion apertures, can accommodate one or more axially concentric sets of balloon catheters therethrough. Thus, a smaller catheter is capable of passing through the apertures of the larger due to the latter's ring-like nature. This smaller catheter may be used for a second procedure behind the first angioplasty area of the perfusion balloon, which then functions as a flexible, hollow, working channel with an inflatable wall. Uses for the second, smaller catheter can include, for example, distal protection against emboli and related particulate matter, additional distal angioplasty and/or stenting, pressure monitoring, or other procedure. This concentric catheter approach also allows additional treatment within the first angioplasty area occupied by the perfusion balloon. For example, the second catheter can be disposed inside the perfusion balloon to conduct ultrasonic, radiation, laser, thermal or other related treatment. Other options include the ability of the catheter to accept drugs, for example, a drug that would inhibit restenosis, or a stent for a more permanent repair of the body lumen.

According to a fourth embodiment of the invention, a method of performing a PTCA with an improved flexibility balloon catheter is disclosed. The method includes the steps of inserting a balloon catheter into a body lumen, advancing the balloon catheter through the body, positioning the balloon catheter adjacent a predetermined location within the body lumen (such as a lesion), and inflating the plurality of expandable chambers. The balloon is configured according to the first and second embodiments described above. The improved flexibility attendant to the separate chambers separated by the flexibly compliant links ensures that the path formed by the lumen will be mimicked by the balloon catheter, even if the path is a tortuous, curved one. This promotes better balloon traversal during the uninflated insertion stage, as well as the improved ability to have a larger portion the balloon catheter engage the inner wall of the body lumen once it has been placed and inflated. As with the first two embodiments, drugs, a stent device and a chamber-enveloping sleeve, or any combination of the three, may optionally be included.

According to a fifth embodiment of the invention, a method of performing a PTCA with an improved flexibility perfusion balloon catheter is disclosed. The method includes the steps of inserting a perfusion balloon catheter into a body lumen, advancing it through the body lumen such that curvature, if any, in the body lumen is mimicked by the perfusion balloon catheter, positioning the perfusion balloon catheter adjacent a predetermined location within the body lumen (such as a lesion), and inflating the perfusion balloon catheter. The configuration is similar to that of the aforementioned third embodiment, where a relatively large perfusion aperture is disposed in donut-like (or ring-like) fashion in each chamber. Axial alignment of the numerous chambers, with their apertures therein, forms a perfusion canal to permit the continued flow of blood, even during balloon inflation. Optionally, drugs and/or stents can be included. In addition, the connection between the channel carrying the pressurized fluid and the flange of the chambers can be integral to promote simple, one-piece construction.

BRIEF DESCRIPTION OF THE DRAWINGS

The following detailed description of the preferred embodiments of the present invention can be best understood when read in conjunction with the following drawings, in which:

FIG. 4a shows a catheter according to a second embodiment of the present invention, with donut-shaped balloon segments having a continuous central perfusion passage, while

DETAILED DESCRIPTION OF THE INVENTION

Figure 1:
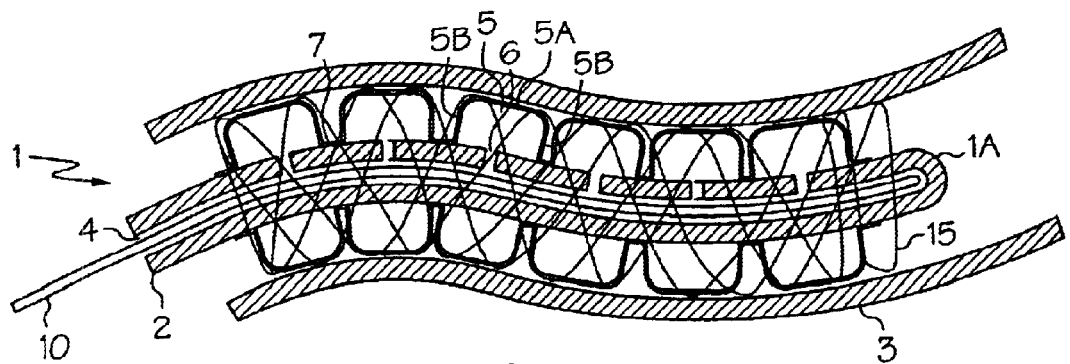
FIG. 1 shows a catheter with a segmented balloon in inflated state according to an embodiment of the present invention, where the balloon is surrounded by a conventional stent, and both inserted into a body lumen with the help of a guide wire.

Referring first to FIG. 1, a balloon catheter 1 with core 2 in a curved body lumen 3, such as an artery, is shown. In the center of the core 2 of catheter 1 is a pressure plenum (also known as a hollow central region) 4 that allows fluid to be pumped from a proximal end (not shown) of the catheter 1 to a distal end 1A. A series of balloon chambers 5 are situated near distal end 1A of catheter 1 and are in fluid communication with the pressure plenum 4 via side branch (also known as radially mounted) apertures 6 that penetrate core 2. The apertures 6 are axially spaced along the core 2 such that a pressurized fluid (for example, an aqueous saline solution) can be delivered to each in a substantially parallel, rather than series, arrangement. The chambers 5 can be inflated by introducing high pressure fluid into pressure plenum 4. Each of the chambers 5 include a radially outward surface 5A that, upon inflation, is adapted to engage the inner wall of the body lumen 3, and a pair of axially spaced flanges 5B. The shape of each chamber 5, including preferential bends or creases, can be determined beforehand, created with an appropriate mold device. Additional lumens can be added in catheter 1, such as for a guide wire 10. Prior to inflation, the balloon chambers 5 are in a collapsed state, for example folded tightly around catheter core 2. In this state, the flexibility within the catheter 1 is mostly determined by the bending properties of core 2, as the balloon chambers 5 in the collapsed state do not significantly add to the overall stiffness of the catheter 1. The improved flexibility inherent in the present segmented design ensures that the "backbone" of catheter 1, defined by the separate chambers 5 connected by flexibly compliant links 7 therebetween, will mimic the shape of the lumen that the catheter 1 is being advanced through. This is especially beneficial when the catheter 1 is traversing a tortuous, highly curved lumen path. Upon inflation of the chambers 5, the overall flexibility is enhanced for the segmented balloon over that of a conventional single chamber balloon due to the presence of the flexibly compliant links 7 situated between adjacent chambers 5. As shown in the present figure, the flexibly compliant links 7 take on the form of a hinge, which is defined by the intersection of core 2 and opposing flanges 5B from two adjacent chambers 5. In a preferred embodiment, all of the chambers 5 are made from one long continuous piece of expandable material. Under the inflated condition shown in the figure, the difference in flexibility between balloon catheter 1 and conventional single balloon catheters is very pronounced; whereas a single balloon becomes a hard, straightened, rigid cylindrical body, the series of short, rigid chambers 5 linked by the hinged central catheter core 2 making up segmented balloon catheter 1 act semi-autonomously, allowing the balloon catheter 1 more freedom to mimic, or substantially conform to, the shape of the inner wall of lumen 3. Variation of the length of these hinges 7 (discussed in more detail below) can also be used to determine the adaptability of the device. Another important parameter is the angle over which the hinges 7 can be bent before the inflated balloon segments come into interference contact with each other. An expanded conventional stent 15 is shown encasing the balloon catheter 1.

Figure 2:
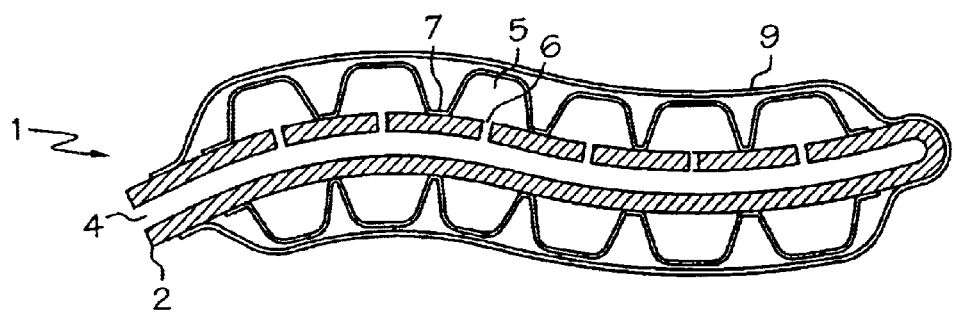
FIG. 2 shows a variation on the first embodiment, with shorter hinge sections.

Referring now to FIG. 2, a variation of the balloon catheter 1, without the stent or guide wire, is shown. The catheter 1 is similar to that shown in FIG. 1, save the length of the hinges 7 disposed on the central catheter core 2. The length of the hinges 7 can be varied, thus leading to a catheter 1 with further improved adaptability, depending on the required level of flexibility, which could be adapted to the different thickness of various anatomic lumen. For example, the use of short hinges 7 results in substantially trapezoid-shaped chambers 5. This configuration possesses an intermediate degree of flexibility and adaptability, larger than that for a conventional single-balloon alternative. In addition, the outer surface of the balloon chambers 5 can be surrounded with a flexible sleeve 9, which can produce several advantages. First, the outer surface of the inflated, as well as the deflated catheter 1 can be tailored to a desired level of smoothness. Second, the effective compression force of the sleeve 9 on the underlying balloon chambers 5 can reduce the deflated size and the time required to deflate the catheter 1 after the procedure. Third, the sleeve 9 will give a more even radial pressure to the body lumen 3 wall and any stent that has to be placed there. Additionally, the friction between the sleeve 9 and a stent (shown in FIG. 1) can also be tailored, depending on specific needs. One way to accomplish this is to have the material of the sleeve 9 be different from the underlying balloon. Thus, for example, if the sleeve 9 needs to be more elastic and less pressure resistant, a wider range of safe, cost-effective material choices might be available. Accordingly, sleeve 9 can be configured to be expansibly responsive to outward-acting pressure coming from the pressurized fluid via individual chambers 5. Furthermore, sleeve 9 may be embedded with drugs, which can be released from the surface of the sleeve with a controlled speed, in order to treat the inner wall of the lumen 3. By way of example, drugs that prevent the occurrence of restenosis, such as sirolimus, can be embedded in sleeve 9, which could be equipped with ample porosity to better accept the drug on the surface. Additionally, in configurations where sleeve 9 is not employed, the drug can be applied directly to the balloon to effect the same type of drug delivery. Either the sleeved or sleeveless configurations allow for the prolonged release of the drug to prevent the formation of undesirable tissue at the site of the lumen reopening.

Figure 3:
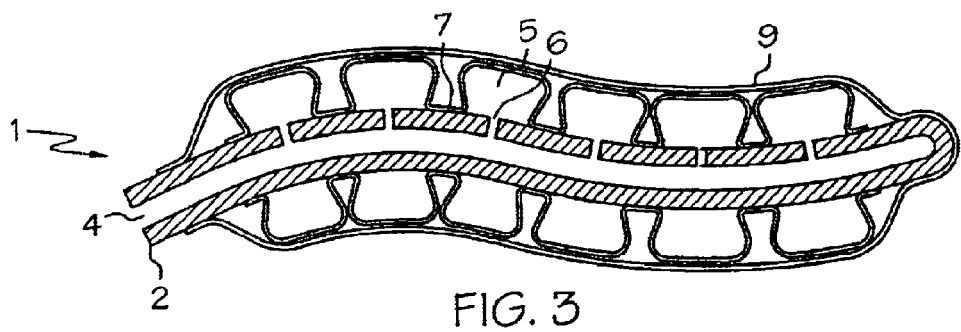
FIG. 3 shows a variation on the first embodiment, with longer hinge sections.

Referring now to FIG. 3, another variation of the balloon catheter 1 is shown. The shape of each balloon chamber 5 is adapted to have a longer hinge 7 than that of FIGS. 1 and 2. In this variation, each balloon chamber 5 has tapered flanges 5B that make an angle of less than 90 degrees with the central axis such that the chamber 5 has less axial length closer to the central axis of the pressure plenum 4 than they do toward the chamber periphery. This creates additional axial room for hinges 7, without interfering with or influencing the outer geometry of the inflated balloon assembly. The longer hinges 7 give a much higher initial flexibility than for the catheter of FIG. 2. As before, a sleeve 9 may be used to regain a more or less continuous cylindrical outer surface. As noted at FIG. 1, the improved adaptability is restricted for bending over a specific angle, until adjacent balloon chambers 5 touch each other. Thus, the geometry of the flanges facilitates a wide range of permissible angles through which the hinges 7 can be bent. It is specifically noted that the angular relationship between successive flange faces does not detract from such flanges being in substantially axial alignment with one another. In other words, as regards the present invention, the outward-facing flange surface cants caused by the generally trapezoidal or mushroom shape of the inflated chambers shown in FIGS. 2 and 3 are not destructive of a substantially axial alignment as long as the chambers to which the flanges are part of follow a straight or body lumen-defined path. The balloons shown in the present figures do not include perfusion features, their use instead being for rapid angioplasty or quick stent placement, where the need for perfusion is of less importance. Similarly, in body lumens requiring extreme small sizes and/or very high pressures, it may be impossible to provide such balloons with a perfusion aperture or canal.

Figure 4A:
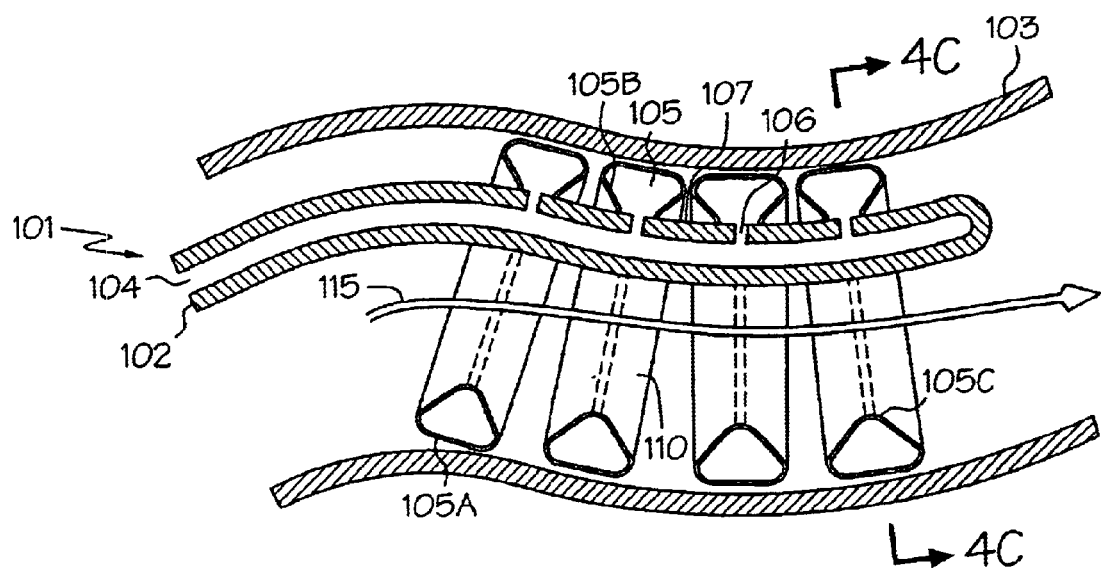
Figure 4B:
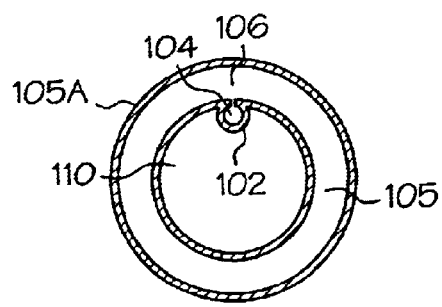
FIG. 4b shows a cutaway view taken along line I—I of FIG. 4a, and FIG. 4c showing a variation of the central perfusion passage and pressure plenum of the embodiment shown in FIG. 4b.
Figure 4C:
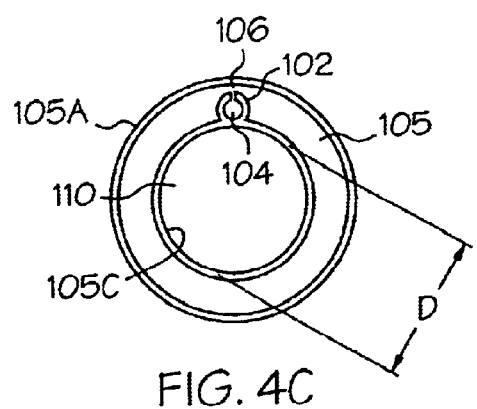

Referring now to FIGS. 4a–4c, the distal end of a segmented perfusion balloon catheter 101 according to another embodiment of the invention is shown. As shown in FIG. 4a, an eccentric core 102 with internal pressure plenum 104 is shown in an artery 103. The catheter 101 extends in a substantially axial direction parallel to the central axis of pressure plenum 104. Each of the tapered donut-shaped balloon chambers 105 have a large central perfusion aperture 110 to facilitate the axial flow of blood through the inflated catheter 101. Because of the tapered flanges 105B and the short axial length of each balloon chamber 105, the fluid pressure will not cause a closure of a perfusion canal (the path of which is shown by arrow 115) defined by the substantially axially aligned apertures 110. This produces the opposite of the clamping effect caused by the inflatable swimming wings used for small children, which are designed to expand inward upon inflation to better grip a child's arm. By contrast, the present cross sectional configuration ensures the continued viability of the individual apertures 110 and collective canal 115. As with the previous embodiment, each of the fluid supply side branch apertures 106 is substantially aligned with of one the balloon chambers 105 such that pressurized fluid supply can enter each chamber 105. An alternative configuration (not shown) could include a direct connection between the donut-shaped chambers 105 in a flange-to-flange arrangement, with an angular offset for the side branch apertures 106. Referring now with particularity to FIGS. 4b and 4c, the pressure plenum 104 connects with the flanges (not presently shown) of the donut-shaped chambers 105, and includes small side branch apertures 106, creating a fluid supply as shown in FIG. 4b, where the pressure plenum 104 extends just along the inside surface 105C of the donut-shaped chambers. In comparison with the embodiment in FIG. 4c, the perfusion aperture 110 could have enhanced producability attributes. The position of pressure plenum 104 closer to the central axis may also further improve the overall flexibility in comparison to FIG. 4c by lowering the overall moment of inertia of the assembly. The alternate approach shown with particularity in FIG. 4c has the core 102 in the interior of each donut-shaped chamber 105. Core 102 and pressure plenum 104 are disposed outside the perfusion aperture 110 with diameter D and leaves the latter completely open to facilitate maximum blood flow therethrough. Thus, the configuration of FIG. 4c, while not possessive of the same producability or moment of inertia benefits as that of FIG. 4b, includes a larger effective opening, thus promoting more complete perfusion of blood.

Figure 5A:
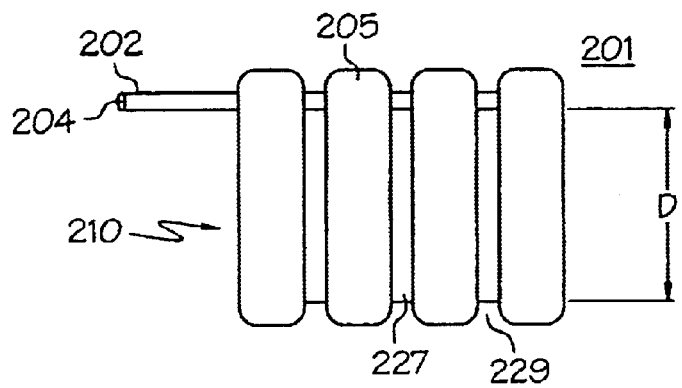
FIGS. 5a and 5b give schematic side views of devices according to another embodiment of the present invention.
Figure 5B:
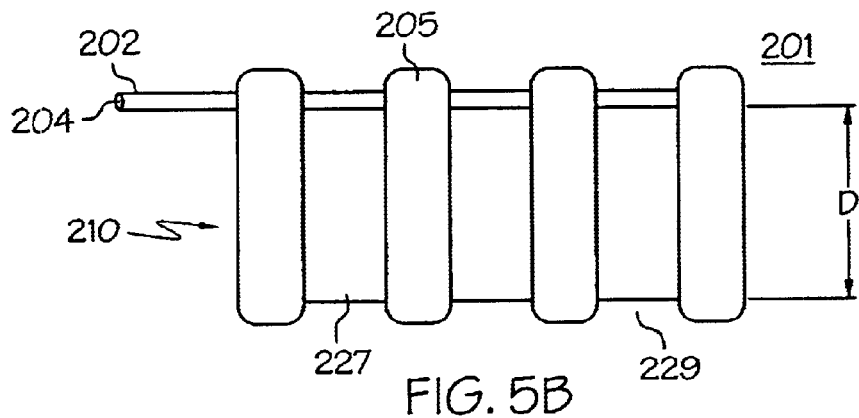

Referring now to FIGS. 5a and 5b, two variations of a segmented perfusion balloon catheter 201 according to the present invention are shown. The construction of the devices in FIGS. 5a and 5b are somewhat similar to that of FIG. 4a–4c in that all include a generally eccentric pressurized fluid supply and a relatively large central perfusion aperture; however, the connection between the chambers in the devices of FIGS. 5a and 5b is augmented by interchamber webs, whereas in the device of FIGS. 4a–4c, the only coupling is through the flexibly compliant links on the fluid supply that are disposed between the chambers. Two variations of the present device are shown in a side view, after inflation. FIG. 5a shows with particularity a device with an eccentric core 202 with internal pressure plenum 204 connected directly to a relatively rigid assembly of donut-shaped balloon chambers 205 without the need for separate hinge sections. Instead, overall balloon connectivity is maintained with interchamber webs 227. Selective radial cutouts 229 from some of the interchamber webs 227 can be used to tailor balloon flexibility and adaptability. As with the previous embodiment, diameter D defines the size of the perfusion aperture 210. FIG. 5b shows perfusion balloon catheter 201 where the sealed sections are much wider so that the distance between the donut balloon chambers 205 becomes larger. Accordingly, it will be appreciated by those skilled in the art that axial spacing can be varied to produce different levels of flexibility within the catheter 201. As with the device shown in FIG. 5a, cutouts 229 within interchamber webs 227 will further improve the flexibility and adaptability.

Figure 6:
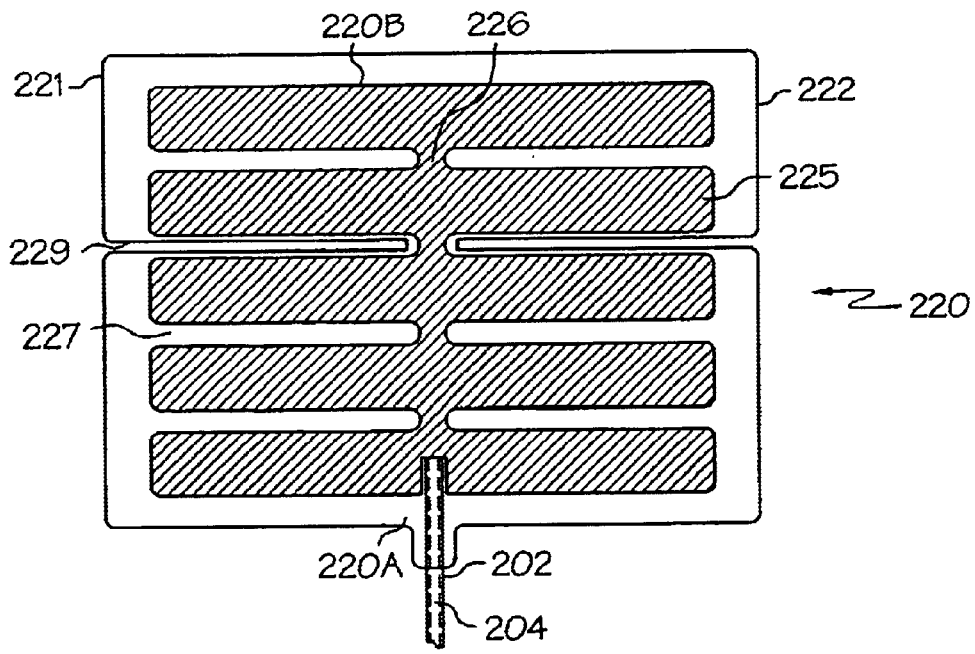
FIG. 6 shows an example of how the embodiment of FIGS. 5a and 5b can be produced from two polymer sheets that are sealed in a specific pattern.

Referring now to FIG. 6, a balloon catheter according to an embodiment depicted in either FIGS. 5a or 5b can be produced from two flat sheets 220 (only one of which is shown) that are sealed in a specific pattern. The sheets 220 are preferably a polymer material with good elastic and biocompatible properties. The sealing technique, which is well known in for the production of inflatable canvas air mattresses, is an inexpensive and reliable method to make inflatable chambers 205 and to create connecting channels between these chambers. Two flat sheets 220, placed on top of each other, are sealed in a pattern that determines the dimensions, position, and flexibility of the final inflatable and non-inflatable sections. Panels 225 form the inner surface of balloon chambers 205, where connecting channels 226 make up a fluid communication path that connects all of the chambers 205. Although shown as axially aligned, the channels 226 do not have to be positioned in the center, and also need not be placed in a straight line, but may be placed with some offset relative to each other. The aforementioned cutouts 229 may later be made to add flexibility to interchamber web 227, which in turn imparts additional flexibility to balloon catheter 201. The geometry of these cutouts 229 can be of any kind and are not limited to the straight cut as shown in FIG. 6. Dependant on the desired flexibility, the cutouts can have a pattern similar to that of stents. Lateral opposing edges 221 and 222 of the flat sheets 220 can be sealed together to create the balloon catheter 201. For example, flat sheet 220 can become cylindrical by connection of the edges 221 and 222 to each other. The balloon catheter 201, now a cylindrical device, will be connected to a fluid supply pressure plenum 204 in tubular central core 202 that is in open fluid communication with the unsealed intermediate channels 226. This pressure plenum 204 may be sealed at once to the cylindrical angioplasty device, while the latter is sealed, but it can also be attached later. The dimensions and arrangement of the connecting channels 226 between the adjacent donut-shaped balloon chambers 205 can be chosen so that the inflation of the complete device performs in a gradual way, where an inflation gradient runs from the proximal end 220A to the distal end 220B of catheter 201. Placement of a stent also becomes more gradual and therefore controllable with such a segmented balloon. Again, as with the previous embodiments, the outer surface of the cylindrical device of FIGS. 5–6 may be embedded with drugs for treatment of the inner wall of the body lumen.

It will be appreciated by those skilled in the art that, unlike the flexible balloons shown in FIGS. 1–3, the perfusion balloons, by virtue of their large apertures that enable continued blood flow, can stay in a patient's body for protracted periods of time, and that after such extended period, the balloon can be deflated and removed. This can be of great benefit in lengthy surgical procedures, including diagnostics and related treatment, such as local drug delivery.

Having described the invention in detail and by reference to preferred embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

We claim:

1. A balloon for use as a surgical device in a body lumen, said balloon comprising:
    an axially elongate tubular core, said core comprising:
        a proximal end configured to be in fluid communication with a pressurizable fluid source;
        a distal end;
        a hollow central region extending from said proximal end to said distal end; and
        a plurality of axially spaced apertures each of which extends from said hollow central region to an outer radial surface of said axially elongate tubular core, each of said axially spaced apertures defining a fluid communication path therethrough;
    a plurality of expandable chambers disposed on said outer radial surface such that each of said chambers is in fluid communication with said hollow central region through at least one of said plurality of axially spaced apertures, each of said plurality of chambers is defined by an outer surface that comprises:
        a body lumen inner wall engaging portion; and
        a pair of flange portions, each extending from said body lumen inner wall engaging portion; and
    a plurality of flexibly compliant links, at least one of which is disposed between adjacent chambers to effect improved flexibility of said balloon and possessive of an axial length such that upon inflation of said balloon, opposing said flange portions between axially adjacent chambers are farther apart near said flexibly compliant link than they are near said body lumen inner wall engaging portion.

2. A balloon according to claim 1, wherein said plurality of expandable chambers are axially adjacent one another.

3. A balloon according to claim 1, wherein said flexibly compliant links are hinges.

4. A balloon according to claim 1, wherein said plurality of expandable chambers and said plurality of flexibly compliant links are made from a single piece of material.

5. A balloon according to claim 4, wherein said material is of substantially constant thickness throughout said plurality of chambers and flexibly compliant links.

6. A balloon according to claim 1, wherein at least a portion of said plurality of expandable chambers are enveloped within an axially elongate flexible sleeve.

7. A balloon according to claim 1, further comprising a drug disposed on at least a portion of said balloon such that, upon insertion of said balloon into a predetermined location within said body lumen, said drug is situated adjacent said predetermined location.

8. A balloon according to claim 7, wherein said drug is a restenosis inhibitor.

\* \* \* \* \*